(12) United States Patent
Hoppe et al.

(10) Patent No.: US 9,919,071 B2
(45) Date of Patent: Mar. 20, 2018

(54) SPILL/LEAK RESISTANT SEAL FOR A WICKING DEVICE

(75) Inventors: Christopher S. Hoppe, Milwaukee, WI (US); Jason L. Halonen, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 2141 days.

(21) Appl. No.: 13/004,978

(22) Filed: Jan. 12, 2011

(65) Prior Publication Data
US 2011/0168802 A1 Jul. 14, 2011

Related U.S. Application Data (60) Provisional application No. 61/294,340, filed on Jan. 12, 2010.

(51) Int. Cl.
*A61L 9/12* (2006.01)

(52) U.S. Cl.
CPC ......... *A61L 9/127* (2013.01); *A61L 2209/133* (2013.01); *A61L 2209/134* (2013.01)

(58) Field of Classification Search
CPC .... A61L 9/127; B65D 47/2031; B05B 11/047
USPC .............................. 239/44, 47; 222/212, 490
See application file for complete search history.

(56) References Cited

U.S. PATENT DOCUMENTS

| 2,644,663 | A | * | 7/1953 | Klingler | 137/846 |
|---|---|---|---|---|---|
| 3,724,756 | A | * | 4/1973 | Maltenfort | 239/47 |
| 3,822,720 | A | * | 7/1974 | Souza | 137/846 |
| 4,928,881 | A | | 5/1990 | Barlics et al. | |
| 5,005,737 | A | * | 4/1991 | Rohr | 222/212 |
| 5,242,111 | A | | 9/1993 | Nakoneczny et al. | |
| 5,342,584 | A | | 8/1994 | Fritz et al. | |
| 5,749,520 | A | | 5/1998 | Martin et al. | |
| 5,782,409 | A | | 7/1998 | Paul | |
| 6,450,375 | B1 | * | 9/2002 | Hins et al. | 222/491 |
| 6,921,025 | B2 | * | 7/2005 | Hart et al. | 239/45 |
| D561,929 | S | | 2/2008 | Meeker et al. | |
| D565,239 | S | | 3/2008 | Meeker et al. | |
| D565,783 | S | | 4/2008 | Meeker et al. | |
| D575,899 | S | | 8/2008 | Meeker et al. | |
| D576,759 | S | | 9/2008 | Meeker et al. | |
| 7,441,755 | B2 | | 10/2008 | O'Leary et al. | |
| 7,568,913 | B2 | | 8/2009 | Decker et al. | |
| D612,976 | S | | 3/2010 | Meeker et al. | |
| D616,139 | S | | 5/2010 | Meeker et al. | |
| D616,594 | S | | 5/2010 | Meeker et al. | |

(Continued)

FOREIGN PATENT DOCUMENTS

| EP | 1702512 | 9/2006 |
|---|---|---|
| JP | 1996-282200 U1 | 5/1998 |

(Continued)

*Primary Examiner* — Ryan A Reis (57) ABSTRACT

A sealing member is disclosed for use with a wick of a diffuser, or the like. The sealing member seals a vessel containing a liquid in a fluid chamber. The sealing member may be composed of a malleable material that may also be resistant to a liquid fragrance contained in the vessel. The sealing member may include a body, flaps and an opening for receiving a wick therethrough. The sealing member may form a persistent seal when a wick is inserted therethrough, while at the same time allowing venting to the fluid chamber.

20 Claims, 5 Drawing Sheets (56) References Cited

U.S. PATENT DOCUMENTS

| | | |
|---|---|---|
| 7,744,232 B2 | 6/2010 | Gruenbacher et al. |
| D630,370 S | 1/2011 | Meeker et al. |
| 2007/0125874 A1 | 6/2007 | Alexander |
| 2007/0237498 A1 | 10/2007 | Helf et al. |
| 2008/0130266 A1 | 6/2008 | DeWitt et al. |
| 2009/0045266 A1 | 2/2009 | Feriani et al. |

FOREIGN PATENT DOCUMENTS

| | | |
|---|---|---|
| JP | 1999-019200 U1 | 8/2000 |
| WO | WO 2004/006968 A1 | 1/2004 |
| WO | WO 2005/077426 A1 | 8/2005 |
| WO | WO 2007/106547 A2 | 9/2007 |
| WO | WO 2009/092135 A1 | 7/2009 |

\* cited by examiner

FIG. 9 ns SPILL/LEAK RESISTANT SEAL FOR A
WICKING DEVICE

CROSS REFERENCE TO RELATED APPLICATION

This patent application claims the benefit under 35 USC 119(e) of U.S. Provisional Patent Application No. 61/294,340, filed on Jan. 12, 2010.

FIELD OF THE DISCLOSURE

The present disclosure pertains to seals, and more particularly, to spill and/or leak resistant seals for wicking devices.

BACKGROUND OF THE DISCLOSURE

Among the different types of fragrance emitters currently available, the passive designs of diffusers are increasingly gaining more consumer attention. Such diffusers generally provide a liquid fragrance and a reed or comparable wicking device that is exposed to its environment to passively and slowly emit the fragrance over time. Inexpensive refills along with extra reeds or wicks may be readily available for purchase. In addition to providing pleasant aesthetics, ease of use and cost-effectiveness are among some other factors for the growing popularity of such diffusers.

However, one substantial drawback associated with passive diffusers pertains to the containment of the liquid fragrance. Typically, the refill or vessel holding the liquid fragrance of such a diffuser is open and exposed to allow a consumer to place as many reeds or wicks into the fragrance as he or she pleases. As such, currently existing diffusers filled with liquid fragrances are prone to spilling once tipped over, shaken, or the like. There is no effective seal which resists such spillage or leakage while also providing a passage through which reeds or wicks are inserted. Although some seals exist which prevent leakage of a fragrance prior to initial use, once such seals are removed or broken, there is nothing to resist spills or leaks during normal usage. Further, some seals may deteriorate over time from persistently being in contact with a fragrance.

Based on the foregoing it can be seen that a need exists for a seal for a wicking device of a diffuser which resists spills or leaks therefrom. There is also a need for a seal which prevents leaks of refill containers prior to initial use, but that allows for venting and continues to provide an effective seal during normal use. Additionally, there is a need for a seal composed of a material that is unaffected by the liquid fragrance being used.

SUMMARY OF THE DISCLOSURE

In accordance with one aspect of the disclosure, a sealing member is disclosed. The sealing member may comprise a body including a plurality of flaps movable between a first position and a second position. When in the second position, the flaps may define an opening through the body. Each flap may have a sealing surface configured to receive and seal against an inserted wick while forming a vent through the body.

In accordance with another aspect of the disclosure, a diffusing apparatus is disclosed. The apparatus may comprise a vessel and a sealing member. The vessel may substantially enclose a fluid chamber and may have a top defining an orifice therethrough into the fluid chamber. The sealing member may cover the orifice, and may comprise a body including a plurality of flaps movable between a first position and a second position. The flaps in the second position may define an opening through the body and orifice into the fluid chamber. Each flap may have a sealing surface configured to receive and seal against an inserted wick while forming a vent through the body and orifice into the fluid chamber.

In accordance with a further aspect of the disclosure, a method of sealing a liquid in a vessel is disclosed. The method may comprise providing a wick, a vessel containing a liquid and having a top defining an orifice therethrough, and a sealing member covering the orifice. The sealing member may comprise a flexible body including a plurality of flaps movable between a first position and a second position. The method may further comprise moving the flaps into the second position by inserting a portion of the wick through the sealing member and the orifice into the liquid contained in the vessel, forming, between the wick and the sealing member, a vent extending through the sealing member and the orifice into the vessel, and sealing the liquid in the vessel.

These and other aspects in this disclosure will become more readily apparent upon reading the following detailed description when taken in conjunction with the accompanying drawings.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions, and equivalents falling with the scope of the present invention.

DETAILED DESCRIPTION

The present disclosure provides a sealing member for use with a diffusing apparatus or the like having a wick, wicking device or reed (collectively, "wick") and vessel. More specifically, the sealing member may be disposed over an orifice in the vessel or refill container of such a diffusing apparatus and may be configured to prevent or resist the contents of the vessel or refill container from spilling or leaking, when the vessel or refill container is tipped over, shaken, or the like.

Figure 1:
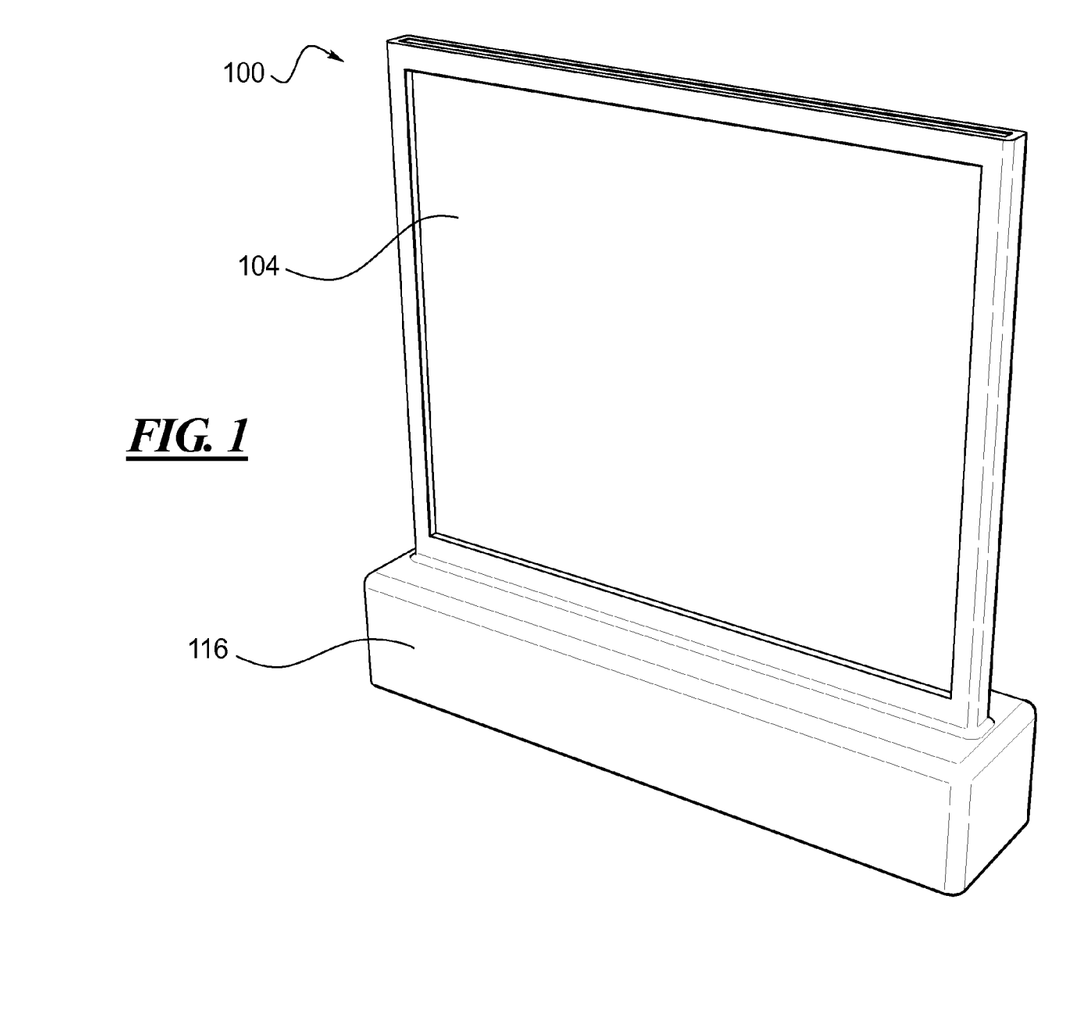
FIG. 1 is a perspective view of an exemplary diffusing apparatus having an exemplary sealing member constructed in accordance with the teachings of the disclosure.
Figure 2:
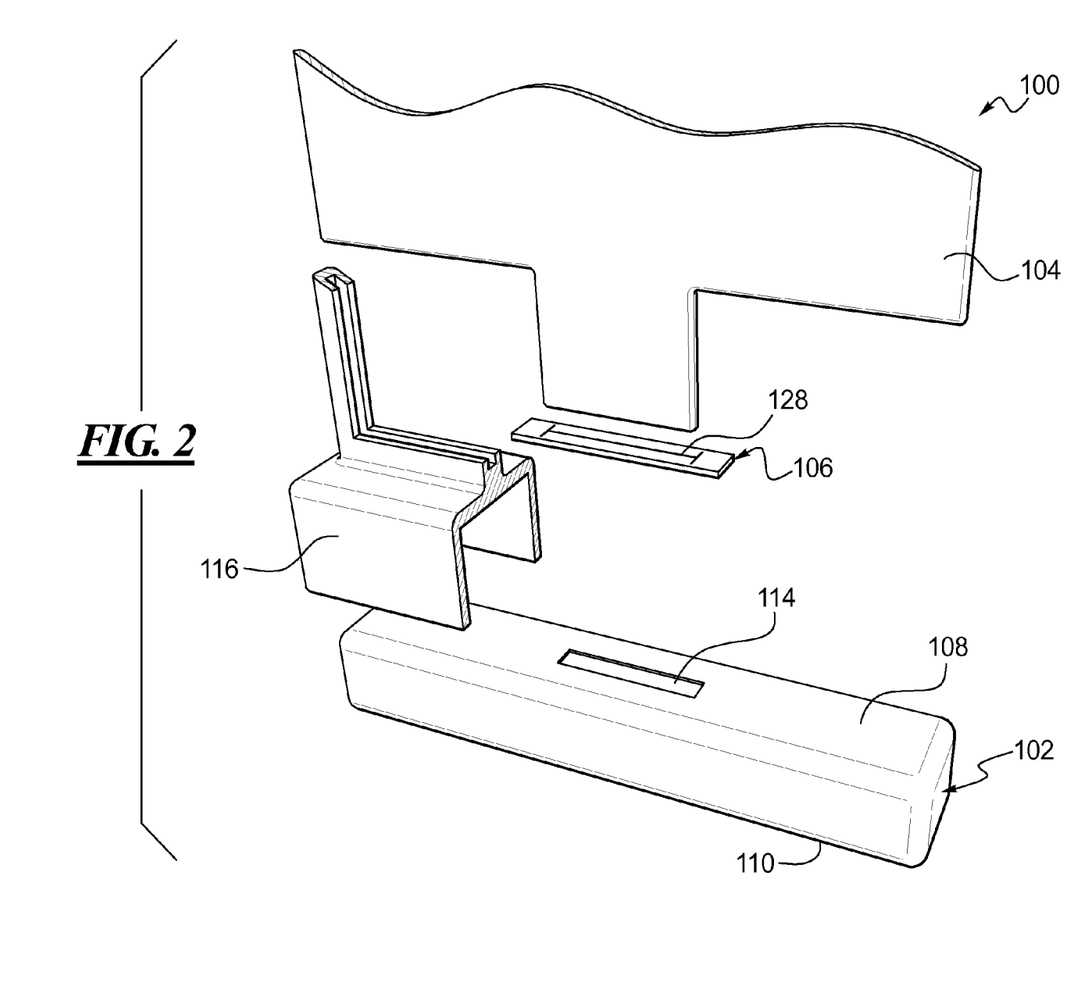
FIG. 2 is an exploded cut away view of the exemplary diffusing apparatus of FIG. 1.
Figure 3:
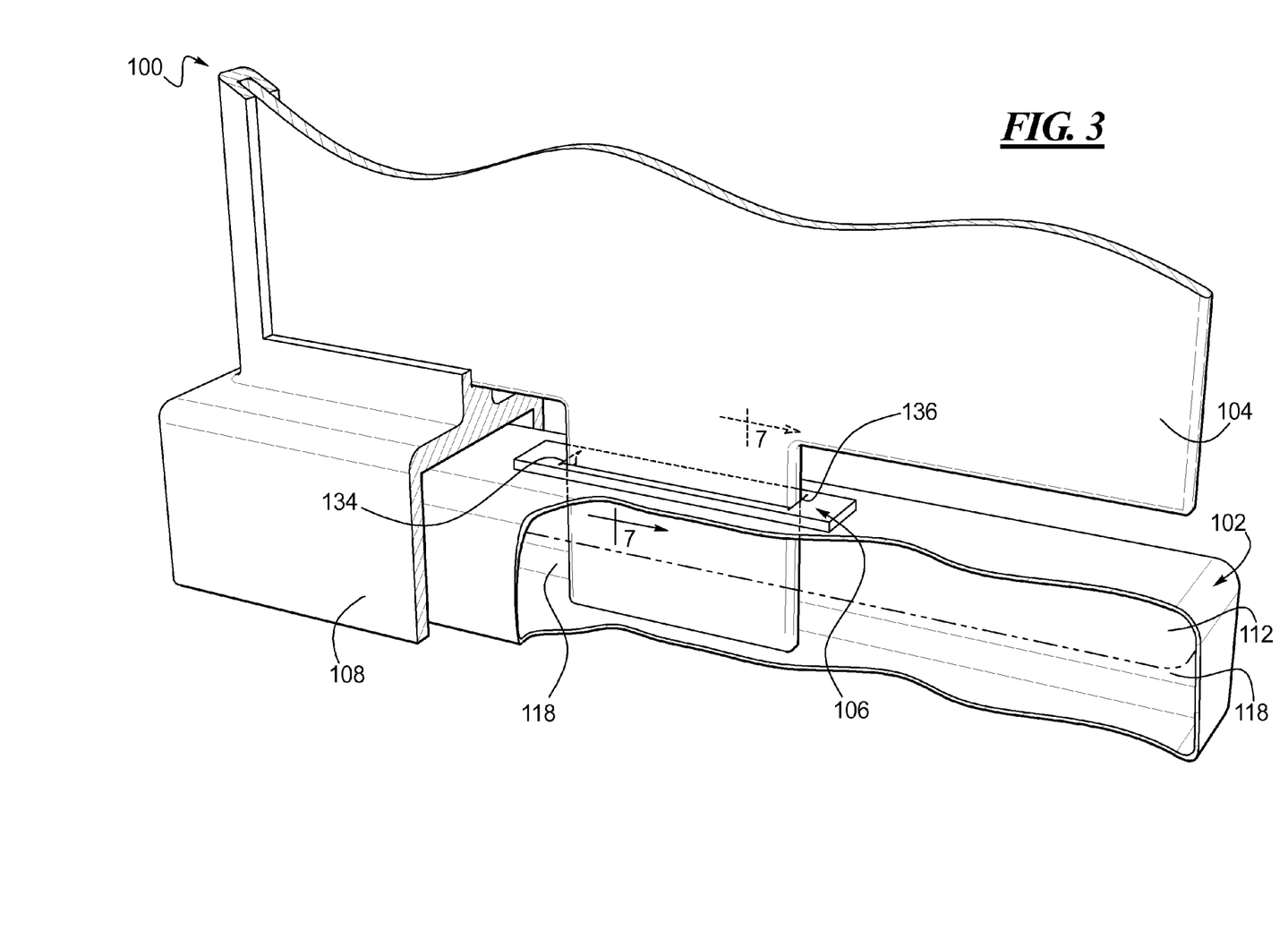
FIG. 3 a cut-away view of the exemplary diffusing apparatus FIG. 1.

FIGS. 1-3 illustrate an exemplary diffusing apparatus 100 comprising a vessel 102, a wick 104 and a sealing member 106. The vessel 102 may have a top 108 and a bottom 110 and may substantially enclose a fluid chamber 112. The top 108 of the vessel 102 may define an orifice 114 therethrough into the fluid chamber 112. The vessel 102 may contain in the fluid chamber 112 fragrance, air freshener, active material or other liquid (collectively, "liquid") desired to be diffused into the air.

A wick 104 may be disposed partially in the liquid 118 contained in the fluid chamber 112 and partially outside of the vessel 102. The liquid 118 may be drawn up the wick 104 and diffused to the air outside of the vessel 102, as is known in the art. The wick may be comprised of plastic, natural materials such as wood or cotton, or may be a synthetic, for example polyester.

The diffusing apparatus may in some embodiments also comprise a cover 116 disposed over some or all of the vessel 102 and wick 104. In some embodiments, the cover 116 may support the wick 104 and/or vessel 102.

The sealing member 106, or "seal," may be disposed on the vessel 102 covering the orifice 114. In one embodiment, the sealing member 106 may be adhered to the top 108 of the vessel 102. In another embodiment, the sealing member 106 may be interference fit in the top 108 of the vessel 102, as is known in the art.

The sealing member 106 may provide a flexible or an initially breakable opening 128 therein through which a wick may be inserted. The sealing member 106 and the associated opening 128 may be configured to receive a wick in any number of ways including, but not limited to, the configurations as taught by U.S. Pat. No. 7,441,755, the contents of which are incorporated herein by reference.

Figure 4:
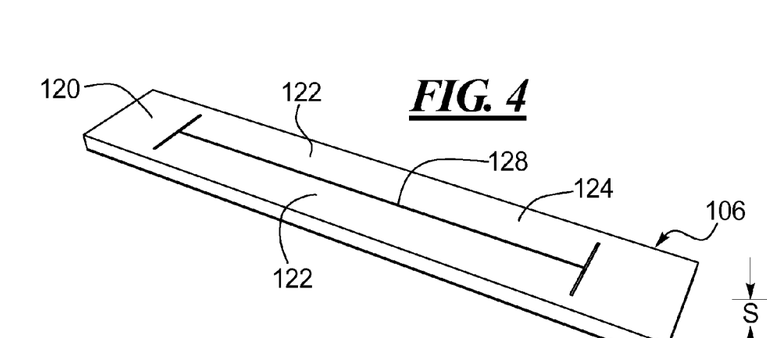
FIG. 4 is a perspective view of one embodiment of the sealing member in accordance with the teachings of the disclosure.
Figure 5:
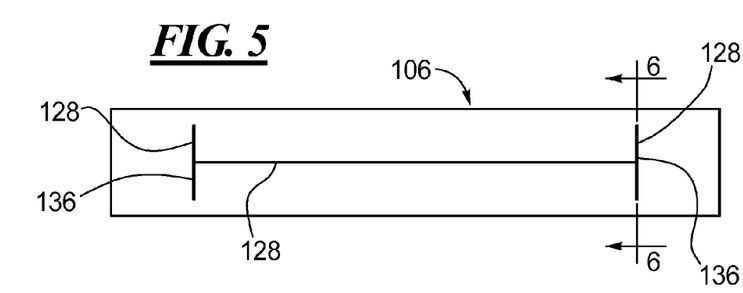
FIG. 5 is a plan view of the sealing member of FIG. 4.
Figure 6:
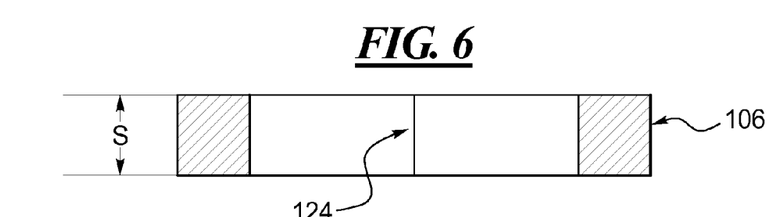
FIG. 6 is a sectional view of the sealing member, along the lines 6-6 in FIG. 5.

FIGS. 4-6 illustrate one embodiment of the sealing member 106. The sealing member 106 may comprise a body 120 including a plurality of flaps 122 movable between a first position 124 and a second position 126 (see FIG. 7). When in the first position 124 (FIGS. 2 and 4-6), the sealing member 106 may be substantially planar and may be disposed parallel to a surface of the vessel 102, such as the top 108 surface. The flaps 122 may be so aligned over the orifice 114 to open into the orifice 114 when the flaps 122 are moved to the second position 126 (FIG. 7).

The flaps 122 may define an opening 128 through which a portion of the wick 104 may be inserted through the body 120 and the orifice 114 and into the fluid chamber 112. In one embodiment, when the flaps 122 are in the first position 124, the opening 128 may be a slit that may be substantially H-shaped. In another embodiment, the opening 128 may be a wave shape or other appropriate shape. In yet another embodiment, the opening 128 may be an H-shaped slot instead of a slit, or the opening 128 may be H-shaped with a portion of the H-shape a slit and a portion a slot. When the flaps 122 are disposed in the first position 124, the shape of the opening 128 is not limited to an H-shape or to the dimensional width of a slit or a slot; other appropriate shapes and widths of the opening 128 may be used without departing from the spirit of the disclosure.

Figure 7:
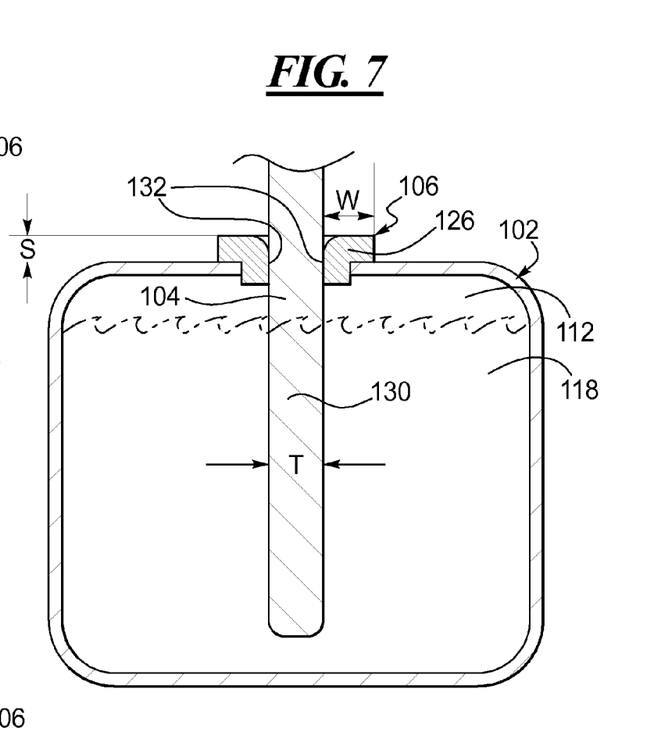
FIG. 7 is a sectional view of the sealing member, vessel and wick, along the lines 7-7 in FIG. 3.

FIG. 7 illustrates an embodiment of a sealing member 106 with an exemplary wick 104 inserted therethrough into the fluid chamber 112 of a vessel 102 containing a liquid 118 to be diffused. The portion of the wick 104 so inserted may be referred to herein as the dipping portion 130 of the wick 104. The flaps 122 of the sealing member 106 are shown in FIG. 7 in one embodiment of the second position 126. As can be seen in FIG. 7, when the dipping portion 130 of the wick 104 is inserted through the opening 128 in the sealing member 106, the flaps 122 may be biased to the second position 126 by the dipping portion 130 of the wick. Each flap 122 may have a sealing surface 132 that receives and seals against the outside surface of the inserted dipping portion 130 of the wick 104. The dipping portion of the wick 104 may fit snugly against substantially all or most of the surfaces of the sealing member 106 that are in contact with the wick 104 such as the sealing surfaces 132 of the flaps and a portion of each side surface 136 of the sealing member 106. A persistent seal may be formed such that if the vessel is tipped on its side, as shown in FIG. 9, the seal formed by the sealing member 106 prevents or resists the liquid 118 in the fluid chamber 112 from leaking out of the vessel 102 through the opening 128 in the sealing member 106.

The dimensions of the wick and seal are of importance and lend to improved diffusion and spill avoidance when selected within ranges identified by the inventors. For example, in an embodiment, the fill index (T/S) may be in the range of about 0.001 to about 100 wherein T is the wick thickness and S is the sealing member thickness. In an embodiment, the gap index (T/W) may be in the range of about 0.001 to about 50 wherein T is the wick thickness and W is the seal width. The seal width W may be measured from the perimeter of the sealing member 106 across a flap 122 to the inserted wick 104, as illustrated in FIG. 7. The flap index (S/W), in an embodiment, may in the range of about 0.001 to about 50, wherein S is the sealing member thickness and W is the seal width.

Figure 8:
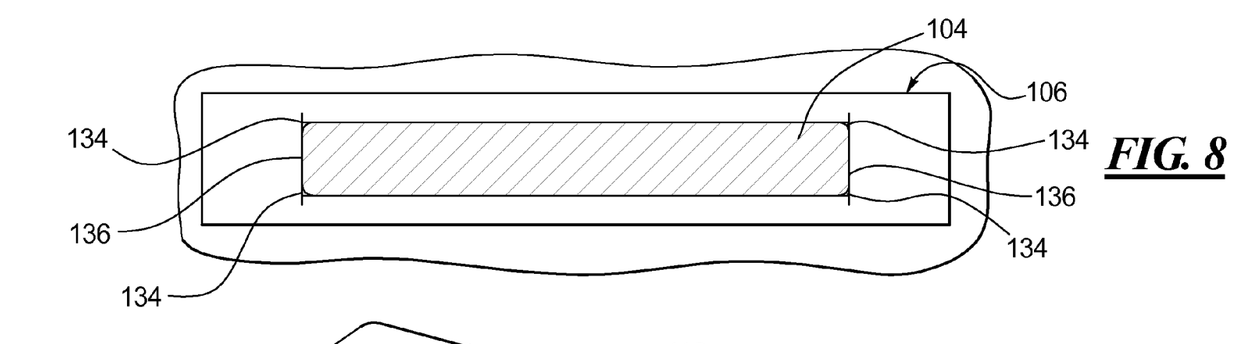
FIG. 8 is a sectional view of the sealing member and wick, along the lines 8-8 in FIG. 9.

As illustrated in FIG. 8, the sealing member 106 may be configured to form at least one vent 134 when the wick is received in the opening 128 of the sealing member 106. When the flaps 122 are disposed in the second position 126, an air vent 134 may be formed by the sealing member 106 and extend through the sealing member 106 and the orifice 114 and into the fluid chamber 112 of the vessel 102. The vent 134 aids in the drawing of the liquid 118 up the wick 104 for diffusion into the surrounding atmosphere. In an embodiment, the dimensions of the vent 134 may be such that the largest diameter of the vent may be greater than zero to about 0.010 inches (or 0.0254 centimeters).

Figure 9:
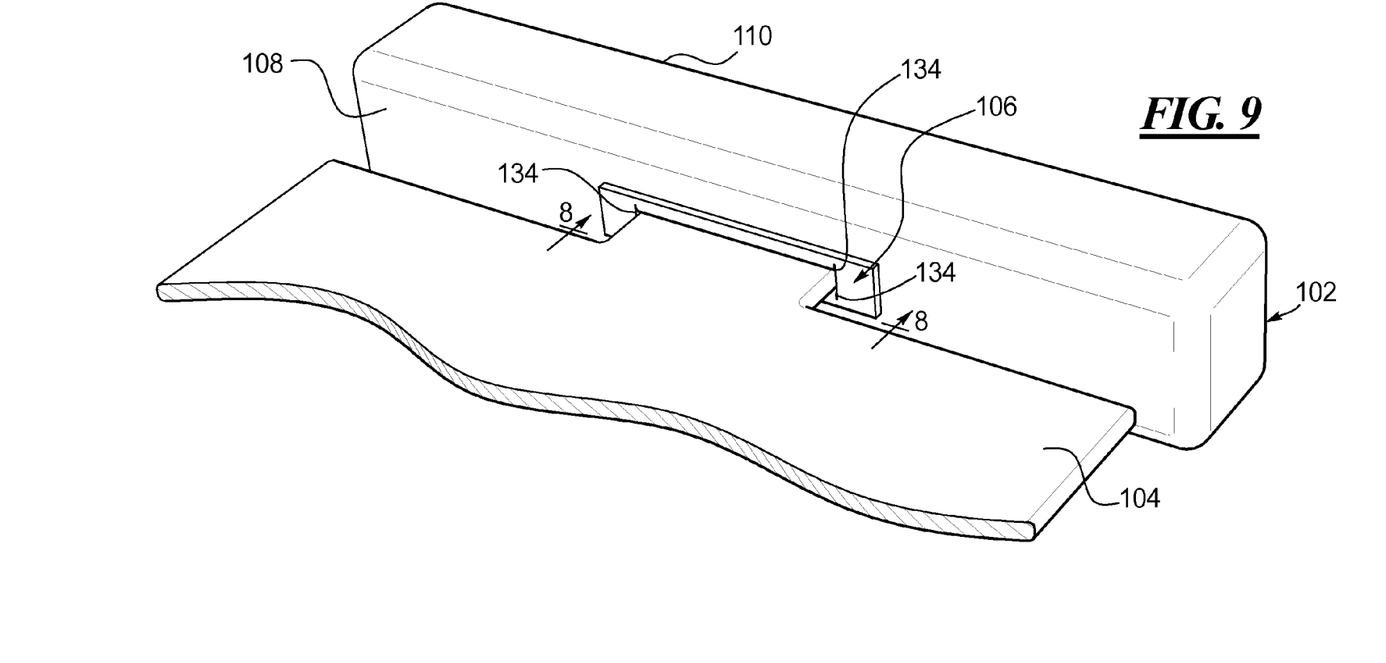
FIG. 9 is a perspective view of an embodiment of the sealing member, wick and vessel rotated so that the vessel is lying on its side.

In the event 134 that the vessel 102 is tipped over on its side as illustrated in FIG. 9, the size of the diameter of the vent 134, in conjunction with the surface tension of the liquid 118, keeps or resists droplets of the liquid 118 from leaking out of the vessel 102 through the vent 134. In one embodiment, the vent 134 may be substantially triangular in shape with a height (or diameter) in the range of greater than zero to about 0.010 inches (or 0.0254 centimeters). In other embodiments, other shapes may be used for the vent 134. In the embodiment illustrated in FIGS. 3 and 8-9, a plurality of vents 134 may be formed when the flaps 122 move to the second position 126. For example, in an exemplary embodiment shown in FIGS. 3 and 8-9, a vent 134 is formed in each of the four corners of the sealing member 106.

The sealing member 106 may be composed of a material that is substantially resistant to the fragrance contained in the vessel 102, which it serves to seal, so as to prevent deterioration of the sealing member 106.

The opening 128 may be configured to be sealed shut prior to initial use. In some embodiments, the opening 128 of the sealing member 106 may be "breakable" meaning that the opening 128 may need to be initially punctured or broken open to allow for the initial or first-time insertion of a wick 104 and/or to allow for venting. In such an arrangement, a portion of each flap 122 may be broken away from the body 120 in order to move the flaps 122 from the first position 124 to the second position 126. In such embodiments where the opening 128 is breakable, the sealing member 106 may be reused to provide a seal around a different wick 104 after the original wick 104 is removed. Such reuse of the sealing member 106, generally does not require the opening 128 to be punctured or broken open again prior to the insertion of a replacement wick 104. Such a sealing member 106 with a breakable opening 128 provides a leak-tight seal (regardless of whether the sealing member 106 is used with the initial wick 104 or a subsequent replacement wick 104) that prevents or resists the leaking of the liquid 118 out of the opening 128 should the vessel 102 be shaken or tipped over. In an embodiment, a sealing member 106 with a breakable opening 128 may be made of polypropylene, polyethylene, polyamide, or other chemically resistant resins that may be sheared without much stretching. In one embodiment, the durometer of such a material may be in the range of about 10 to about 100 Shore A. In another embodiment, the durometer of such a material may be in the range of about 70 to about 100 Shore A. In another embodiment, the durometer of such a material may be in the range of about 10 to about 50 Shore D. In yet another embodiment, the durometer of such a material may be in the range of about 22 to about 50 Shore D.

In other embodiments, the opening 128 of the sealing member 106 may not need to be punctured for first-time or initial use but the sealed opening 128 may be pushed open by the insertion of the wick 104 therethrough, regardless of whether it is the first time a wick 104 is inserted or a subsequent insertion of a replacement wick 104 after the initial wick 104 has been removed. In an embodiment, the material from which the sealing member 106 may be made may be sufficiently resilient and elastic and the durometer of the material may be such that the opening 128 reseals itself after the removal of an inserted wick 104.

Such a sealing member 106 with a resealing opening 128 provides a leak-tight seal that prevents or resists the leaking of the liquid 118 out of the opening 128 should the vessel 102 be shaken or tipped over. A leak-tight seal may be provided on the vessel 102 regardless of whether the sealing member 106 is used with the initial wick 104, a subsequent replacement wick 104 or in the absence of a wick (for example, after the removal of an inserted wick 104). In an embodiment, a sealing member 106 with a resealing opening 128 may be made of a silicone rubber, thermoplastic elastomer, thermoplastic olefin or comparable material with a durometer in the range of about 30 to about 100 Shore A.

In operation, when a sealing member 106 made of a resealing material is used, a wick 104 may be inserted into a vessel 102 by moving the flaps 122 from the first position 124 into the second position 126 by inserting the dipping portion 130 of the wick 104 through the opening 128 in the sealing member 106 and through the orifice 114 into the liquid 118 contained in the vessel 102. The position of the flaps 122 of the sealing member 106 may form a vent 134 between the wick 104 and the sealing member 106. The vent 134 may extend through the sealing member 106 and the orifice 114 into the vessel 102. The sealing surface of each flap 122 may be disposed against the wick 104 and may form a persistent seal that resists or prevents spilling or leaking of the liquid, when the vessel is tipped over, shaken, or the like. In some embodiments, the flaps 122 may conform to the shape of the wick 104. After removal of the inserted wick 104, the sealing member 106 may return to the first position 124 from the second position 126 and the opening 128 may be sealed shut such that the sealing member 106 resists or prevents spilling or leaking of the liquid when the vessel 102 is tipped over, shaken, or the like. The sealing member 106 may be reused with another wick 104 in the same way as described above.

In operation, when a sealing member 106 has a breakable opening 128, the opening 128 may be initially punctured open. The flaps 122 may then be moved from the first position 124 into the second position 126 by inserting the dipping portion 130 of the wick 104 through the broken opening 128 in the sealing member 106 and through the orifice 114 into the liquid 118 contained in the vessel 102. The position of the flaps 122 of the sealing member 106 may form a vent 134 between the wick 104 and the sealing member 106. The vent 134 may extend through the sealing member 106 and the orifice 114 into the vessel 102. The sealing surface of each flap 122 may be disposed against the wick to form a persistent seal that resists or prevents spilling or leaking of the liquid, when the vessel is tipped over, shaken, or the like. After removal of the wick 104 from the sealing member 106, the sealing member 106 with an initially breakable opening 128 may be reused with another wick 104 in the same way as described above except that, once initially broken, the opening may not need to be broken again for subsequent use with a replacement wick 104.

The use of the terms "a", "an","the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

INDUSTRIAL APPLICABILITY

The sealing member may be used to seal an orifice of a vessel of a diffusing apparatus. A wick may be inserted through the sealing member into liquid contained in the vessel. The sealing member may be configured to seal against the inserted wick so that the liquid in the vessel is prevented or resisted from spilling or leaking, when the vessel is tipped over, shaken, or the like.

What is claimed is:
1. A sealing member comprising a body including a plurality of flaps movable between a first position and a second position, the flaps in the second position defining an opening through the body, each flap having a sealing surface configured to receive and seal against an inserted wick while forming a vent through the body.

2. The sealing member of claim 1, wherein the sealing member is comprised of a thermoplastic elastomer.

3. The sealing member of claim 1, wherein the sealing member is comprised of a thermoplastic olefin.

4. The sealing member of claim 1, wherein the sealing member is comprised of silicone.

5. The sealing member of claim 1, wherein the sealing member is fragrance resistant.

6. The sealing member of claim 1, wherein the plurality of flaps in the first position define a substantially H-shaped slit.

7. The sealing member of claim 1, wherein the vent is substantially triangular in shape.

8. The sealing member of claim 1, wherein the sealing member is substantially planar when the flaps are disposed in the first position.

9. The sealing member of claim 1, wherein the sealing member is resilient and has a durometer of about 30 to about 100 Shore A.

10. The sealing member of claim 1, wherein a portion of each flap is breakable from the body.

11. An apparatus comprising:
 a vessel substantially enclosing a fluid chamber, the vessel having a top defining an orifice therethrough into the fluid chamber; and
 a sealing member covering the orifice, the sealing member comprising a body including a plurality of flaps movable between a first position and a second position, the flaps in the second position defining an opening through the body and orifice into the fluid chamber, each flap having a sealing surface configured to receive and seal against an inserted wick while forming a vent through the body and orifice into the fluid chamber.

12. The apparatus of claim 11, wherein the sealing member is adhered to the top of the vessel.

13. The apparatus of claim 11, wherein the sealing member is interference fit in the top of the vessel.

14. The apparatus of claim 11, wherein the sealing member is fragrance resistant.

15. The apparatus of claim 11, wherein the plurality of flaps in the first position define a substantially H-shaped slit.

16. The apparatus of claim 11 wherein the wick is inserted through the opening and orifice into the fluid chamber, wherein the apparatus has a gap index in the range of about 0.001 to about 50.

17. The apparatus of claim 11 wherein the wick is inserted through the opening and orifice into the fluid chamber, wherein the apparatus has a flap index in the range of about 0.001 to about 50.

18. The apparatus of claim 11, wherein at least a portion of each flap is breakable from the body.

19. The apparatus of claim 11 wherein the wick is inserted through the opening and orifice into the fluid chamber, wherein the apparatus has a fill index in the range of about 0.001 to about 100.

20. A method of sealing a liquid in a vessel, the method comprising:
 providing a wick, a vessel containing a liquid and having a top defining an orifice therethrough, and a sealing member covering the orifice, the sealing member comprising a flexible body including a plurality of flaps movable between a first position and a second position;
 moving the flaps into the second position by inserting a portion of the wick through the sealing member and the orifice into the liquid contained in the vessel;
 forming, between the wick and the sealing member, a vent extending through the sealing member and the orifice into the vessel; and
 sealing the liquid in the vessel.

\* \* \* \* \*